US006926911B1

(12) United States Patent
Boucher, Jr.

(10) Patent No.: US 6,926,911 B1
(45) Date of Patent: Aug. 9, 2005

(54) COMPOUNDS AND METHODS FOR THE TREATMENT OF AIRWAY DISEASES AND FOR THE DELIVERY OF AIRWAY DRUGS

(75) Inventor: Richard C. Boucher, Jr., Chapel Hill, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 0 days.

(21) Appl. No.: 09/465,429

(22) Filed: Dec. 21, 1999

Related U.S. Application Data

(60) Provisional application No. 60/137,991, filed on Jun. 7, 1999, provisional application No. 60/113,785, filed on Dec. 22, 1998.

(51) Int. Cl.[7] ..................... A61K 33/42; A61K 33/14; A61K 33/04; A61K 31/70; A61K 31/4965
(52) U.S. Cl. .................... 424/601; 424/677; 424/709; 514/46; 514/45; 514/255.06; 514/851
(58) Field of Search ............................ 424/45, 46, 601, 424/677, 709; 514/851, 255.06, 46, 45

(56) References Cited

U.S. PATENT DOCUMENTS

| | | | |
|---|---|---|---|
| 4,826,679 A | 5/1989 | Roy | |
| 5,162,348 A | 11/1992 | Glass | |
| 5,182,299 A | 1/1993 | Gullans et al. | 514/460 |
| 5,441,938 A | 8/1995 | Speert et al. | |
| 5,441,983 A | 8/1995 | Hwang et al. | |
| 5,516,798 A | 5/1996 | Ferket | |
| 5,569,450 A | 10/1996 | Duan et al. | 424/45 |
| 5,607,691 A | 3/1997 | Hale et al. | 424/449 |
| 5,628,984 A | 5/1997 | Boucher, Jr. | |
| 5,725,841 A | 3/1998 | Duan et al. | 424/45 |
| 5,817,028 A | 10/1998 | Anderson | 600/529 |
| 5,837,226 A * | 11/1998 | Jungherr et al. | 424/78.1 |
| 5,863,563 A | 1/1999 | Scheele | |
| 5,876,700 A * | 3/1999 | Boucher, Jr. et al. | 424/45 |
| 5,880,098 A | 3/1999 | Häussinger | 514/23 |

FOREIGN PATENT DOCUMENTS

| | | |
|---|---|---|
| WO | WO 91/14435 A1 | 10/1991 |
| WO | WO 97/38686 A1 | 10/1997 |
| WO | WO 97/48679 A1 | 12/1997 |
| WO | WO 99/61012 A2 | 12/1999 |
| WO | WO 99/61012 A3 | 12/1999 |

OTHER PUBLICATIONS

PCT Search Report for PCT/US99/30585.
Handler et al.; *Kidney Cell Survival in High Tonicity*, Comp. Biochem. Physiol. 117A, No. 3:301-304 (1997).
Travis et al.; *Activity of Abundant Antimicrobials of the Human Airway*, Am. J. of Resp. Cell and Molecular Biol. 20:872-878 (1999).
Burg, *Molecular basis of osmotic regulation*, Walter B, Cannon Lecture pp. F983-F996 (1995).

Communication with Supplementary Partial European Search Report, EP 99 96 8166, Aug. 4, 2003.
Aitken et al., *Analysis of Sequential Aliquots of Hypertonic Saline Solution-Induced Sputum From Clinically Stable Patients with Cystic Fibrosis*, Chest, vol. 123, No. 3, Mar. 2003, pp. 792-799.
De Boeck et al., *Sputum Induction in Young Cystic Fibrosis Patients*, European Respiratory Journal, vol. 16, 2000, pp. 91-94.
Eng et al., *Short-Term Efficacy of Ultrasonically Nebulized Hypertonic Saline in Cystic Fibrosis*, Pediatric Pulmonology, vol. 21, 1996, pp. 77-83.
Henig et al., *Sputum Induction As a Research Tool for Sampling the Airways of Subjects With Cystic Fibrosis*, Thorax, vol. 56, 2001, pp. 306-311.
Hjalmarsen et al., *Sex hormone responses in healthy men and male patients with chronic obstructive pulmonary disease during an oral glucose load*, Scand. J. Clin. Lab. Invest., vol. 56, No. 7, Nov. 1996, pp. 635-640.
Knowles et al, *Activation by extracellular nucleotides of chloride secretion in the airway epithelia of patients with cystic fibrosis*, New England Journal of Medicine, vol. 325, No. 8, Aug. 22, 1991, pp. 575-577.
McShane et al., *Airway surface pH in subjects with cystic fibrosis*, Eur. Respir. J., vol. 21, 2003, pp. 37-42.
Olivier et al., *Acute safety and effects on mucociliary clearance of aerosolized uridine 5'-triphosphate +/- amiloride in normal human adults*, Am., J. Respir. Crit. Care Med., vol. 154, No. 1, Jul. 1996, pp. 217-223.
Robinson et al., *Effect of Hypertonic Saline, Amiloride, and Cough on Mucociliary Clearance in Patients With Cystic Fibrosis*, American Journal of Respiratory and Critical Care Medicine, vol. 153, 1996, pp. 1503-1509.
Rodwell et al., *Airway Responsiveness to Hyperosmolar Saline Challenge in Cystic Fibrosis: A Pilot Study*, Pediatric Pulmonology, vol. 21, 1996, pp. 282-289.

(Continued)

*Primary Examiner*—Shengjun Wang
(74) *Attorney, Agent, or Firm*—Myers Bigel Sibley & Sajovec

(57) ABSTRACT

Chronic obstructive airway diseases are treated by administering an osmotically active compound such as a salt, sugar, sugar alcohol, or organic osmolyte to the afflicted airway surface. The compound may be administered as a liquid or dry powder aerosol formulation. Diseases that can be treated by the method include cystic fibrosis, chronic bronchitis, and ciliary dyskinesia. The formulations of the invention can also be used in conjunction with other active agents such as bronchodilators, sodium channel blockers, antibiotics, enzymes, or purinoceptor agonists on airway surfaces.

5 Claims, No Drawings

OTHER PUBLICATIONS

Rubin et al., *Iodinated glycerol has no effect on pulmonary function, symptom score, or sputum properties in patients with stable chronic bronchitis*, Chest, vol. 109, No. 2, Feb. 1996, 348(5), 5 pp.

Sagel et al., *Induced Sputum Inflammatory Measures Correlate With Lung Function in Children With Cystic Fibrosis*, The Journal of Pediatrics, vol. 141, No. 6, Dec. 2002, pp. 811-817.

Schuller-Levis et al., *Taurine protects rat bronchioles from acute ozone-induced lung inflammation and hyperplasia*, Experimental Lung Research, vol. 21, 1995, pp. 877-888.

Cropp, *Effectiveness of Brochodilators in Cystic Fibrosis*, The American Journal of Medicine, vol. 100, Supp. 1A, 1996, pp. 19s-29s.

\* cited by examiner

COMPOUNDS AND METHODS FOR THE TREATMENT OF AIRWAY DISEASES AND FOR THE DELIVERY OF AIRWAY DRUGS

STATEMENT OF PRIORITY

This application claims priority from U.S. Provisional Patent Application Ser. No. 60/137,991 filed Jun. 7, 1999 and from U.S. Provisional Patent Application Ser. No. 60/113,785 filed Dec. 22, 1998, which are incorporated herein in their entirety.

STATEMENT OF FEDERAL SUPPORT

This invention was made with government support under Grant No. HL34322 from the National Institutes of Health. The United States Government has certain rights in this invention.

FIELD OF THE INVENTION

This invention relates to methods and compositions useful for hydrating airway surfaces.

BACKGROUND OF THE INVENTION

Chronic obstructive pulmonary diseases are characterized by the retention of mucous secretions in the lungs. Examples of such diseases include cystic fibrosis, chronic bronchitis, and primary or secondary ciliary dyskinesia. Such diseases affect approximately 15 million patients in the United States, and are the sixth leading cause of death. Other airway or pulmonary diseases characterized by the accumulation of retained mucous secretions include sinusitis (an inflammation of the paranasal sinuses associated with upper respiratory infection) and pneumonia.

U.S. Pat. No. 5,817,028 to Anderson describes a method for the provocation of air passage narrowing (for evaluating susceptibility to asthma) and/or the induction of sputum in subjects. It is suggested that the same technique can be used to induce sputum and promote mucociliary clearance. Substances suggested include sodium chloride, potassium chloride, mannitol and dextrose.

SUMMARY OF THE INVENTION

Certain objects, advantages and novel features of the invention will be set forth in the description that follows, and will become apparent to those skilled in the art upon examination of the following, or may be learned with the practice of the invention.

A first aspect of the present invention is a method for treating chronic, obstructive pulmonary disease in a subject in need of such treatment. The method comprises administering a non-absorbable, osmotically active compound (hereinafter referred to as an "active compound") such as a salt, sugar, sugar alcohol, organic osmolyte, or other osmotically active compound to an airway surface of the subject in an amount effective to increase the volume of fluid on the airway surface.

In one embodiment of the foregoing, a bronchodilator is administered to the patient prior to or concurrently with the active compound to inhibit bronchoconstriction that may be induced by the active compound.

The active compound may be administered as a delayed or controlled release formulation, such as by encapsulating the active compound in liposomes, encapsulating the compound in a biodegradable polymer, etc.

A second aspect of the present invention is a therapeutic method of administering an active agent to an airway surface of a subject in need thereof. The method comprises administering the active agent in an effective therapeutic amount in a vehicle, the vehicle comprising an osmotically active compound of the present invention in an amount effective to increase the volume of liquid on the airway surface.

A third aspect of the present invention is a method for the lavage of the lung of a patient in need thereof. The method comprises administering a liquid comprising an active compound of the present invention to an afflicted portion of the lung of the patient (e.g., a lobe) in an amount effective to wash the afflicted lung portion, the active compound in the solution being present in an amount effective to increase the volume of liquid on the airway surface of the portion of the lung to which the liquid is administered.

Active compounds of the present invention, used either as active compounds alone, or as active compounds used in conjunction with other kinds of active agents (e.g., bronchodilators, purinergic receptors, antibiotics, enzymes, anti-inflammatory agents, etc.), may be administered to airway surfaces (including nasal surfaces) by any suitable means, such as by droplets, sprays, aerosols of respirable or non-respirable particles, or transbronchoscopic lavage. The active compounds of the present invention may be administered in aqueous or non-aqueous (e.g., solid particulate) form.

Formulations of the active compounds of the present invention, either with or without other active ingredients for administration to airway surfaces, are also an aspect of this invention.

The use of an active compound of the present invention for the preparation of a medicament for carrying out the methods described above are also an aspect of this invention.

One object of the methods and formulations described herein is to expand or increase the volume of fluid on airway surfaces, particularly the volume of the periciliary liquid layer, and to thereby increase or facilitate cough clearance, mucociliary clearance, and/or gas-liquid dependent clearance of mucous.

The foregoing and other aspects of the present invention are explained in detail in the specification set forth below.

DETAILED DESCRIPTION OF THE INVENTION

The present invention now will be described more fully hereinafter, in which preferred embodiments of the invention are illustrated. This invention may, however, be embodied in many different forms and should not be construed as limited to the embodiments set forth herein. Rather, these embodiments are provided so that this disclosure will fully convey the scope of the invention to those skilled in the art. Unless otherwise defined, all technical and scientific terms used herein have the same meaning as commonly understood by one of ordinary skill in the art to which this invention belongs. All publications, patent applications, patents, and other references mentioned herein are incorporated by reference in their entirety.

Active compounds of the present invention are molecules or compounds that are osmotically active (i.e., are "osmolytes"). "Osmotically active" compounds of the present invention are membrane-impermeable (i.e., essentially non-absorbable) on the airway or pulmonary epithelial surface. The terms "airway surface" and "pulmonary surface," as used herein, include pulmonary airway surfaces such as the bronchi and bronchioles, alveolar surfaces, and nasal and sinus surfaces. Active compounds of the present invention may be ionic osmolytes (i.e., salts), or may be non-ionic osmolytes (i.e., sugars, sugar alcohols, and organic osmolytes). It is specifically intended that both racemic forms of the active compounds that are racemic in nature are included in the group of active compounds that are useful in the present invention.

Active compounds useful in the present invention that are ionic osmolytes include any salt consisting of a pharmaceutically acceptable anion and a pharmaceutically acceptable cation. Preferably, either (or both) of the anion and cation are non-absorbable (i.e., osmotically active and not subject to rapid active transport) in relation to the airway surfaces to which they are administered. Such compounds include but are not limited to anions and cations that are contained in FDA approved commercially marketed salts, see, e.g., *Remington: The Science and Practice of Pharmacy, Vol. II*, pg. 1457 (19$^{th}$ Ed. 1995), and can be used in any combination including their conventional combinations.

Pharmaceutically acceptable anions that can be used to carry out the present invention include, but are not limited to, acetate, benzenesulfonate, benzoate, bicarbonate, bitartrate, bromide, calcium edetate, camsylate (camphorsulfonate), carbonate, chloride, citrate, dihydrochloride, edetate, edisylate (1,2-ethanedisulfonate), estolate (lauryl sulfate), esylate (1,2-ethanedisulfonate), fumarate, gluceptate, gluconate, glutamate, glycollylarsanilate (p-glycollamidophenylarsonate), hexylresorcinate, hydrabamine (N,N'-Di(dehydroabietyl)ethylenediamine), hydrobromide, hydrochloride, hydroxynaphthoate, iodide, isethionate, lactate, lactobionate, malate, maleate, mandelate, mesylate, methylbromide, methylnitrate, methylsulfate, mucate, napsylate, nitrate, pamoate (embonate), pantothenate, phosphate or diphosphate, polygalacturonate, salicylate, stearate, subacetate, succinate, sulfate, tannate, tartrate, teoclate (8-chlorotheophyllinate), triethiodide, bicarbonate, etc. Particularly preferred anions include sulfate, nitrate, gluconate, iodide, bicarbonate, bromide, and phosphate. In that chloride is absorbed by airway surfaces, it is a less preferred anion.

Pharmaceutically acceptable cations that can be used to carry out the present invention include, but are not limited to, organic cations such as benzathine (N,N'-dibenzylethylenediamine), chloroprocaine, choline, diethanolamine, ethylenediamine, meglumine (N-methyl D-glucamine), procaine, D-Lysine, L-lysine, D-arginine, L-arginine, triethylammonium, N-methyl D-glycerol, and the like. Particularly preferred organic cations are 3-carbon, 4-carbon, 5-carbon and 6-carbon organic cations. Metallic cations useful in the practice of the present invention include but are not limited to aluminum, calcium, lithium, magnesium, potassium, sodium, zinc, iron, ammonium, and the like. Particularly preferred cations include potassium, choline, lithium, meglumine, D-lysine, ammonium, magnesium, and calcium. In that sodium is absorbed by airway surfaces, it is a less preferred cation for the purposes of the present invention. As between the dextrorotatory (D) form and the levorotatory (L) form of an active compound of the present invention, the D-form is preferred.

Specific examples of salts that may be used as active compounds to carry out the present invention include, but are not limited to, potassium chloride, choline chloride, choline iodide, lithium chloride, meglumine chloride, L-lysine chloride, D-lysine chloride, ammonium chloride, potassium sulfate, potassium nitrate, potassium gluconate, potassium iodide, ferric chloride, ferrous chloride, potassium bromide, etc. Either a single salt or a combination of different salts may be used to carry out the present invention. Combinations of different salts are preferred. When different salts are used, one of the anion or cation may be the same among the differing salts.

Active compounds of the present invention also include non-ionic osmolytes such as sugars, sugar-alcohols, and organic osmolytes. Sugars and sugar-alcohols useful in the practice of the present invention include but are not limited to 3-carbon sugars (e.g., glycerol, dihydroxyacetone); 4-carbon sugars (e.g., both the D and L forms of erythrose, threose, and erythrulose); 5-carbon sugars (e.g., both the D and L forms of ribose, arabinose, xylose, lyxose, psicose, fructose, sorbose, and tagatose); and 6-carbon sugars (e.g., both the D and L forms of altose, allose, glucose, mannose, gulose, idose, galactose, and talose, and the D and L forms of allo-heptulose, allo-hepulose, gluco-heptulose, manno-heptulose, gulo-heptulose, ido-heptulose, galacto-heptulose, talo-heptulose). Additional sugars useful in the practice of the present invention include raffinose, raffinose series oligosaccharides, and stachyose. Both the D and L forms of the reduced form of each sugar/sugar alcohol useful in the present invention are also active compounds within the scope of the invention. For example, glucose, when reduced, becomes sorbitol; within the scope of the invention, sorbitol and other reduced forms of sugar/sugar alcohols (e.g., dulcitol, arabitol) are accordingly active compounds of the present invention. As with the ionic osmolytes of the present invention, as between the dextrorotatory (D) form and the levorotatory (L) form of an active compound of the present invention, the D-form is preferred.

Active compounds of the present invention additionally include the family of non-ionic osmolytes termed "organic osmolytes." The term "organic osmolytes" is generally used to refer to molecules used to control intracellular osmolality in the kidney. See e.g., J. S. Handler et al., *Comp. Biochem. Physiol,* 117, 301–306 (1997); M. Burg, *Am. J. Physiol.* 268, F983–F996 (1995). Although the inventor does not wish to be bound to any particular theory of the invention, it appears that these organic osmolytes are useful in controlling extracellular volume on the airway/pulmonary surface. Organic osmolytes useful as active compounds in the present invention include but are not limited to three major classes of compounds: polyols (polyhydric alcohols), methylamines, and amino acids. The polyol organic osmolytes considered useful in the practice of this invention include, but are not limited to, inositol, myo-inositol, and sorbitol. The methylamine organic osmolytes useful in the practice of the invention include, but are not limited to, choline, betaine, carnitine (L-, D- and DL forms), phosphorylcholine, lysophosphorylcholine, glycerophosphorylcholine, creatine, and creatine phosphate. The amino acid organic osmolytes of the invention include, but are not limited to, the D- and L forms of glycine, alanine, glutamine, glutamate, aspartate, proline and taurine. Additional osmolytes useful in the practice of the invention include tihulose and sarcosine. Mammalian organic osmolytes are preferred, with human organic osmolytes being most preferred. However, certain organic osmolytes are of bacterial, yeast, and marine animal origin, and these compounds are also useful active compounds within the scope of the present invention.

Under certain circumstances, an osmolyte precursor may be administered to the subject; accordingly, these compounds are also useful in the practice of the invention. The term "osmolyte precursor" as used herein refers to a compound which is converted into an osmolyte by a metabolic step, either catabolic or anabolic. The osmolyte precursors of this invention include, but are not limited to, glucose, glucose polymers, glycerol, choline, phosphatidylcholine, lyso-phosphatidylcholine and inorganic phosphates, which are precursors of polyols and methylamines. Precursors of amino acid osmolytes within the scope of this invention include proteins, peptides, and polyamino acids, which are hydrolyzed to yield osmolyte amino acids, and metabolic precursors which can be converted into osmolyte amino acids by a metabolic step such as transamination. For example, a precursor of the amino acid glutamine is poly-L-glutamine, and a precursor of glutamate is poly-L-glutamic acid.

Also intended within the scope of this invention are chemically modified osmolytes or osmolyte precursors. Such chemical modifications involve linking to the osmolyte (or precursor) an additional chemical group which alters or enhances the effect of the osmolyte or osmolyte precursor (e.g., inhibits degradation of the osmolyte molecule). Such chemical modifications have been utilized with drugs or prodrugs and are known in the art. (See, for example, U.S. Pat. Nos. 4,479,932 and 4,540,564; Shek, E. et al., *J. Med. Chem.* 19:113–117 (1976); Bodor, N. et al., *J. Pharm. Sci.* 67:1045–1050 (1978); Bodor, N. et al., *J. Med. Chem.* 26:313–318 (1983); Bodor, N. et al., *J. Pharm. Sci.* 75:29–35 (1986);

In general, osmotically active compounds of the present invention (both ionic and non-ionic) that do not promote, or in fact deter or retard bacterial growth are preferred.

The active compounds, methods and compositions of the present invention are useful as therapeutics for the treatment of chronic obstructive airway or pulmonary disease in subjects in need of such treatment. The active compounds, compositions and methods described herein may also be used to induce the production of a sputum or mucous sample in a patient. Additionally, the active compounds, compositions and methods described herein can be used for the lavage of the lungs and/or airways of a patient. The active compounds and compositions described herein may also be administered with other active agents that are to be introduced into airways of a subject, and in fact may function as vehicles or carriers for the other active agents.

Suitable subjects to treated according to the present invention include both avian and mammalian subjects, preferably mammalian. Any mammalian subject in need of being treated according to the present invention is suitable, including dogs, cats and other animals for veterinary purposes. Human subjects are preferred. Human subjects of both genders and at any stage of development (i.e., neonate, infant, juvenile, adolescent, adult) can be treated according to the present invention. Preferred subjects include those humans afflicted with a chronic obstructive airway or pulmonary disease, including but not limited to cystic fibrosis, chronic bronchitis, emphysema, primary and secondary ciliary dyskinesia, sinusitis, and pneumonia. Human subjects afflicted with cystic fibrosis are particularly preferred.

Active compounds disclosed herein may be administered to airway surfaces including the nasal passages, sinuses and lungs of a subject by any suitable means known in the art, such as by nose drops, mists, etc. In one embodiment of the invention, the active compounds of the present invention are administered by transbronchoscopic lavage. In a preferred embodiment of the invention, the active compounds of the present invention are deposited on lung airway surfaces by administering an aerosol suspension of respirable particles comprised of the active compound, which the subject inhales. The respirable particles may be liquid or solid.

Numerous inhalers for administering aerosol particles to the lungs of a subject are known.

Inhalers such as those developed by Inhale Therapeutic Systems, Palo Alto, Calif., USA, may be employed, including but not limited to those disclosed in U.S. Pat. Nos. 5,740,794; 5,654,007; 5,458,135; 5,775,320; and 5,785,049. The Applicant specifically intends that the disclosures of all patent references cited herein be incorporated by reference herein in their entirety. Inhalers such as those developed by Dura Pharmaceuticals Inc, San Diego, Calif., USA, may also be employed, including but not limited to those disclosed in U.S. Pat. Nos. 5,622,166; 5,577,497; 5,645,051; and 5,492,112. Additionally, inhalers such as those developed by Aradigm Corp., Hayward, Calif., USA, may be employed, including but not limited to those disclosed in U.S. Pat. Nos. 5,826,570; 5,813,397; 5,819,726; and 5,655,516. These apparatuses are particularly suitable as dry particle inhalers.

Aerosols of liquid particles comprising the active compound may be produced by any suitable means, such as with a pressure-driven aerosol nebulizer or an ultrasonic nebulizer. See, e.g., U.S. Pat. No. 4,501,729. Nebulizers are commercially available devices which transform solutions or suspensions of the active ingredient into a therapeutic aerosol mist either by means of acceleration of compressed gas, typically air or oxygen, through a narrow venturi orifice or by means of ultrasonic agitation. Suitable formulations for use in nebulizers consist of the active ingredient in a liquid carrier, the active ingredient comprising up to 40% w/w of the formulation, but preferably less than 20% w/w. The carrier is typically water (and most preferably sterile, pyrogen-free water) or a dilute aqueous alcoholic solution. Perfluorocarbon carriers may also be used. Optional additives include preservatives if the formulation is not made sterile, for example, methyl hydroxybenzoate, antioxidants, flavoring agents, volatile oils, buffering agents and surfactants.

Aerosols of solid particles comprising the active compound may likewise be produced with any solid particulate medicament aerosol generator. Aerosol generators for administering solid particulate medicaments to a subject produce particles which are respirable, as explained above, and generate a volume of aerosol containing a predetermined metered dose of a medicament at a rate suitable for human administration. One illustrative type of solid particulate aerosol generator is an insufflator. Suitable formulations for administration by insufflation include finely comminuted powders which may be delivered by means of an insufflator or taken into the nasal cavity in the manner of a snuff. In the insufflator, the powder (e.g., a metered dose thereof effective to carry out the treatments described herein) is contained in capsules or cartridges, typically made of gelatin or plastic, which are either pierced or opened in situ and the powder delivered by air drawn through the device upon inhalation or by means of a manually-operated pump. The powder employed in the insufflator consists either solely of the active ingredient or of a powder blend comprising the active ingredient, a suitable powder diluent, such as lactose, and an optional surfactant. The active ingredient typically comprises from 0.1 to 100% w/w of the formulation. A second type of illustrative aerosol generator comprises a metered dose inhaler. Metered dose inhalers are pressurized aerosol dispensers, typically containing a suspension or solution formulation of the active ingredient in a liquified propellant. During use these devices discharge the formulation through a valve adapted to deliver a metered volume, typically from 10 to 150 µl, to produce a fine particle spray containing the active ingredient. Suitable propellants include certain chlorofluorocarbon compounds, for example, dichlorodifluoromethane, trichlorofluoromethane, dichlorotetrafluoroethane and mixtures thereof. The formulation may additionally contain one or more co-solvents, for example, ethanol, surfactants, such as oleic acid or sorbitan trioleate, antioxidants and suitable flavoring agents.

The aerosol, whether formed from solid or liquid particles, may be produced by the aerosol generator at a rate of from about 10 to 150 liters per minute, more preferably from about 30 to 150 liters per minute, and most preferably about 60 liters per minute. Aerosols containing greater amounts of medicament may be administered more rapidly.

The dosage of the active compounds disclosed herein will vary depending on the condition being treated and the state of the subject, but generally may be from about 0.1 or 1 to about 30, 50 or 100 milliosmoles of the salt, deposited on the airway surfaces. The daily dose may be divided among one or several unit dose administrations.

Other active agents may be administered concurrently to the subject in need thereof with the osmotically active compounds of the present invention. As used herein, the term "concurrently" means sufficiently close in time to produce a combined effect (that is, concurrently may be simultaneously, or it may be two or more events occurring within a short time period before or after each other). When administered with other active agents, the active compounds of the present invention may function as a vehicle or carrier for the other active agent, or may simply be administered concurrently with the other active agent. The active compound of the present invention may be used as a dry or liquid vehicle for administering other active ingredients to airway surfaces. Such other active agents may be administered for treating the disease or disorder for which they are intended, in their conventional manner and dosages, in combination with the active compounds of the present invention, which may be thought of as serving as a vehicle or carrier for the other active agent. Any such other active ingredient may be employed, particularly where hydration of the airway surfaces (i.e., the activity of the osmotically active compounds of the present invention) facilitates the activity of the other active ingredient (e.g., by facilitating or enhancing uptake of the active ingredient, by contributing to the mechanism of action of the other active ingredient, or by any other mechanisms). In a preferred embodiment of the invention, when the active compound of the present invention is administered concurrently with another active agent, the active compound of the present invention has an additive effect in relation to the other active agent; that is, the desired effect of the other active agent is enhanced by the concurrent administration of the active compounds of the present invention.

In particular, bronchodilators may be administered concurrently with the active compounds of the present invention. Bronchodilators that can be used in the practice of the present invention include, but are not limited to, β-adrenergic agonists including but not limited to epinephrine, isoproterenol, fenoterol, albutereol, terbutaline, pirbuterol, bitolterol, metaproterenol, isoetharine, salmeterol, xinafoate, as well as anticholinergic agents including but not limited to ipratropium bromide, as well as compounds such as theophylline and aminophylline. These compounds may be administered in accordance with known techniques, either prior to or concurrently with the active compounds described herein.

Other active ingredients that may be administered with the active compounds of the present invention include ion transport modulators and other active agents known to be useful in the treatment of the subject afflicted with a chronic obstructive pulmonary disease (e.g., DNase, antibiotics, etc.).

Ion transport modulators that can be administered as active agents along with the active compounds of the present invention herein include, sodium channel blockers such as amiloride, benzamil or phenamil, purinoceptor (particularly $P2Y_2$) receptor agonists such as UTP, UTP-γ-S, dinucleotide $P2Y_2$ receptor agonists, and β-agonists. Thus the method of the present invention may be used as a vehicle system to administer the active compounds described in U.S. Pat. No. 5,837,861 to Pendergast et al., U.S. Pat. No. 5,635,160 to Stutts et al., U.S. Pat. No. 5,656,256 to Boucher et al., U.S. Pat. No. 5,292,498 to Boucher et al., and U.S. Pat. No. 4,501,729 to Boucher et al., the disclosures of all of which are to hereby incorporated by reference herein in their entirety.

Other active ingredients that can be administered in combination with the formulations described herein include nucleic acids or oligonucleotides; viral gene transfer vectors (including adenovirus, adeno-associated virus, and retrovirus gene transfer vectors); enzymes; and hormone drugs or physiologically active proteins or peptides such as insulin, somatostatin, oxytocin, desmopressin, leutinizing hormone releasing hormone, nafarelin, leuprolide, adrenocorticotrophic hormone, secretin, glucagon, calcitonin, growth hormone releasing hormone, growth hormone, etc. Enzyme drugs that may be used to carry out the present invention, include but are not limited to DNAse (for the treatment of, e.g., cystic fibrosis), $α_1$-antitrypsin (e.g., to inhibit elastase in the treatment of emphysema), etc. Suitable anti-inflammatory agents, including steroids, for use in the methods of the present invention include, but are not limited to, beclomethasone dipropionate, prednisone, flunisolone, dexamethasone, prednisolone, cortisone, theophylline, albuterol, cromolyn sodium, epinephrine, flunisolide, terbutaline sulfate, alpha-tocopherol (Vitamin E), dipalmitoylphosphatidylcholine, salmeterol and fluticasone dipropionate. Examples of antibiotics that may be employed include, but are not limited to tetracycline, choramphenicol, aminoglycosides, for example, tobramycin, beta-lactams, for example ampicillin, cephalosporins, erythromycin and derivatives thereof, clindamycin, and the like. Suitable anti-viral agents include acyclovir, ribavirin, ganciclovir and foscarnet. Suitable antineoplastic agents include, but are not limited to, etoposid, taxol, and cisplatin. Antihistamines include, but are not limited to, diphenhydramine and ranitadine. Anti- *Pneumocystis carinii* pneumonia drugs such as pentamidine and analogs thereof may also be used. Anti-tuberculosis drugs such as rifampin, erythromycin, chlorerythromycin, etc. Chelators of divalent cations (e.g., EGTA, EDTA), expectorants, and other agents useful in the loosening of mucous secretions (e.g., n-acetyl-L-cysteine) may also be administered as desired in the practice of the present invention.

The present invention is particularly useful for chronic treatments: that is, treatments wherein the administration is repeated two or more times in close proximity to one another, so that the multiple treatments achieve a combined therapeutic effect. For example, the administration may be carried out two, three, four, five, six or seven times a week, on separate days throughout the week. The treatment may be carried out for a period of two, four, or six days or more; daily for two or four weeks or more; daily for two or four months or more. etc. For example, the administering step may be carried out three, four, five or six times a day for the duration of the condition being treated, with chronic conditions receiving chronic treatments.

The compounds, compositions and methods described herein can be used for the lavage of a lung, or lung lobe, in a patient in need thereof by administering an effective therapeutic amount of the compositions to the lung of a subject. Lavage may be carried out with a bronchoscope by instilling a volume of fluid into a desired lobe of the lung (e.g., 30 milliliters to 3 liters, typically 300 milliliters) in accordance with known techniques. Lavage may be single administration or repetitive (e.g., three washings). A portion of the instilled fluid is removed or aspirated, after instillation, in accordance with known techniques. The lavage solution may be an aqueous solution, or may be a perfluorocarbon liquid such as used for blood substitutes.

Solid or liquid particulate pharmaceutical formulations containing active compounds of the present invention should include particles of respirable size: that is, particles of a size sufficiently small to pass through the mouth and larynx upon inhalation and into the bronchi, bronchioles, and (if necessary) the alveoli of the lungs. The bronchioles are a particularly preferred target for delivery to the airway surfaces. In general, particles ranging from about 1 to 5 or 6 microns in size (more particularly, less than about 4.7 microns in size) are respirable. Particles of non-respirable size which are included in the aerosol tend to be deposited in the throat and swallowed, and the quantity of non-respirable particles in the aerosol is preferably minimized. For nasal administration, a particle size in the range of 10–500 $\mu$m is preferred to ensure retention in the nasal cavity.

In the manufacture of a formulation according to the invention, active compounds of the present invention may be admixed with, inter alia, an acceptable carrier. The carrier must, of course, be acceptable in the sense of being compatible with any other ingredients in the formulation and must not be deleterious to the patient. The carrier may be a solid or a liquid, or both, and is preferably formulated with the compound as a unit-dose formulation, for example, a capsule, which may contain from 0.5% to 99% by weight of the active compound. One or more active compounds may be incorporated in the formulations of the invention, which formulations may be prepared by any of the well-known techniques of pharmacy consisting essentially of admixing the components.

Compositions containing respirable dry particles of active compound may be prepared by grinding the active compound with a mortar and pestle, and then passing the micronized composition through a 400 mesh screen to break up or separate out large agglomerates.

The pharmaceutical composition may optionally contain a dispersant which serves to facilitate the formation of an aerosol. A suitable dispersant is lactose, which may be blended with the active agents in any suitable ratio (e.g., a 1 to 1 ratio by weight).

The foregoing is illustrative of the present invention, and is not to be construed as limiting thereof. The invention is defined by the following claims, with equivalents of the claims to be included therein.

That which is claimed is:

1. A method of administering a sodium channel blocker to an airway surface of a subject in need thereof, comprising:

administering the sodium channel blocker in an effective therapeutic amount in a vehicle, said vehicle comprising potassium sulfate or potassium phosphate as an ionic osmolyte, said potassium sulfate or potassium phosphate included in an amount effective to increase the volume of liquid on the airway surface, wherein said subject is afflicted with cystic fibrosis.

2. The method according to claim 1, wherein said administering step is an aerosol inhalation administering step.

3. The method according to claim 1, wherein said vehicle comprises potassium sulfate as the ionic osmolyte.

4. The method according to claim 1, wherein said vehicle comprises potassium phosphate as the ionic osmolyte.

5. The method according to claim 1, wherein said sodium channel blocker is selected from the group consisting of amiloride, benzamil and phenamil.

* * * * *